(12) United States Patent
Yaghi et al.

(10) Patent No.: US 8,709,134 B2
(45) Date of Patent: *Apr. 29, 2014

(54) REVERSIBLE ETHYLENE OXIDE CAPTURE IN POROUS FRAMEWORKS

(75) Inventors: Omar M. Yaghi, Los Angeles, CA (US); David Kyle Britt, Los Angeles, CA (US); Alexander U. Czaja, Dirmstein (DE)

(73) Assignees: The Regents of the University of California, Oakland, CA (US); BASF SE, Ludwigshafen (DE)

( * ) Notice: Subject to any disclaimer, the term of this patent is extended or adjusted under 35 U.S.C. 154(b) by 156 days.

This patent is subject to a terminal disclaimer.

(21) Appl. No.: 13/147,357

(22) PCT Filed: Feb. 1, 2010

(86) PCT No.: PCT/US2010/022777
§ 371 (c)(1),
(2), (4) Date: Oct. 26, 2011

(87) PCT Pub. No.: WO2010/088629
PCT Pub. Date: Aug. 5, 2010

(65) Prior Publication Data
US 2012/0031268 A1 Feb. 9, 2012

Related U.S. Application Data

(60) Provisional application No. 61/149,069, filed on Feb. 2, 2009.

(51) Int. Cl.
*B01D 53/04* (2006.01)

(52) U.S. Cl.
USPC .................. 95/90; 95/900; 96/108; 556/115

(58) Field of Classification Search
USPC .................. 95/90, 96, 900, 902; 96/108, 153; 502/400; 556/115, 132
See application file for complete search history.

(56) References Cited

U.S. PATENT DOCUMENTS

| | | | |
|---|---|---|---|
| 2,684,967 | A | 7/1954 | Berg |
| 4,532,225 | A | 7/1985 | Tsao et al. |
| 5,160,500 | A | 11/1992 | Chu et al. |
| 5,208,335 | A | 5/1993 | Ramprasad et al. |
| 5,648,508 | A | 7/1997 | Yaghi |

(Continued)

FOREIGN PATENT DOCUMENTS

| | | |
|---|---|---|
| DE | 102005023856 A1 | 11/2006 |
| DE | 102005054523 A1 | 5/2007 |

(Continued)

OTHER PUBLICATIONS

Ramos, Ceclilia Giel-Barragan, International Search Report and Written Opinion, PCT/US2010/022777, European Patent Office, Jun. 7, 2010.

(Continued)

*Primary Examiner* — Frank Lawrence, Jr.
(74) *Attorney, Agent, or Firm* — Joseph R. Baker, Jr.; Gavrilovich, Dodd & Lindsey LLP

(57) ABSTRACT

This disclosure relates to porous frameworks for ethylene oxide separation and recovery.

16 Claims, 5 Drawing Sheets

(56) References Cited

U.S. PATENT DOCUMENTS

| | | | |
|---|---|---|---|
| 5,733,505 A | 3/1998 | Goldstein et al. | |
| 6,479,447 B2 | 11/2002 | Bijl et al. | |
| 6,501,000 B1 | 12/2002 | Stibrany et al. | |
| 6,617,467 B1 | 9/2003 | Muller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 * | 8/2005 | Yaghi et al. | 556/46 |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 | 10/2010 | Mueller et al. | |
| 2003/0004364 A1 | 1/2003 | Yaghi et al. | |
| 2003/0078311 A1 | 4/2003 | Muller et al. | |
| 2003/0148165 A1 | 8/2003 | Muller et al. | |
| 2003/0222023 A1 | 12/2003 | Mueller et al. | |
| 2004/0081611 A1 | 4/2004 | Muller et al. | |
| 2004/0225134 A1 | 11/2004 | Yaghi et al. | |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0014371 A1 | 1/2005 | Tsapatsis | |
| 2005/0124819 A1 | 6/2005 | Yaghi et al. | |
| 2005/0154222 A1 | 7/2005 | Muller et al. | |
| 2005/0192175 A1 | 9/2005 | Yaghi et al. | |
| 2006/0057057 A1 | 3/2006 | Muller et al. | |
| 2006/0135824 A1 | 6/2006 | Mueller et al. | |
| 2006/0154807 A1 | 7/2006 | Yaghi et al. | |
| 2006/0185388 A1 | 8/2006 | Muller et al. | |
| 2006/0252641 A1 * | 11/2006 | Yaghi et al. | 502/401 |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |
| 2007/0202038 A1 | 8/2007 | Yaghi et al. | |
| 2008/0017036 A1 | 1/2008 | Schultink et al. | |
| 2008/0184883 A1 | 8/2008 | Zhou et al. | |
| 2008/0190289 A1 * | 8/2008 | Muller et al. | 95/25 |
| 2009/0155588 A1 | 6/2009 | Hesse et al. | |
| 2010/0132549 A1 | 6/2010 | Yaghi et al. | |
| 2010/0143693 A1 | 6/2010 | Yaghi et al. | |
| 2010/0186588 A1 | 7/2010 | Yaghi et al. | |
| 2010/0286022 A1 | 11/2010 | Yaghi et al. | |
| 2011/0137025 A1 | 6/2011 | Yaghi et al. | |
| 2012/0133939 A1 * | 5/2012 | Yaghi et al. | 356/402 |

FOREIGN PATENT DOCUMENTS

| | | |
|---|---|---|
| EP | 1070538 A2 * | 1/2001 |
| EP | 1674555 A1 | 6/2006 |
| WO | 2004101575 A2 | 11/2004 |
| WO | 2006/072573 A2 | 7/2006 |
| WO | 2006116340 A1 | 11/2006 |
| WO | WO 2006/122920 A1 * | 11/2006 |
| WO | 2007101241 A2 | 9/2007 |
| WO | 2007/111739 A2 | 10/2007 |
| WO | 2008091976 A1 | 7/2008 |
| WO | 2008/138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A3 | 12/2009 |
| WO | 2010078337 A1 | 7/2010 |
| WO | 2010083418 A1 | 7/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |

OTHER PUBLICATIONS

Andrew et al., "Post-Synthetic Modification of Tagged MOFs," Angew. Chem. Int. Ed. 47:8482-8486 (2008).

Baharlou, Simin. International Preliminary Report on Patentability for PCT/US2009/046463. Date of Mailing: Dec. 16, 2010.

Banerjee et al., "High-Throughput Synthesis of Zeolitic Imidazolate Frameworks and Application to CO2 Capture," Science 319:939-943 (2008).

Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).

Barman et al., "Azulene Based Metal-Organic Frameworks for Strong Adsorption of H2," Chem. Commun. 46: 7981-7983 (2010).

Barton et al., "Tailored Porous Materials," Chem. Mater. 11:2633-2656 (1999).

Bloch et al., "Metal Insertion in a Microporous Metal-Organic Framework Lined with 2,2'-Bipyridine" J. Am. Chem. Soc. 132:14382-14384 (2010).

Britt et al., "Highly efficient separation of carbon dioxide by a metal-organic framework replete with open metal sites," Proc. Natl. Acad. Sci. USA 106:20637-20640 (2009).

Caskey et al., "Dramatic Tuning of CO2 Uptake via Metal Substitution in a Coordination Polymer with Cylindrical Pores," JACS 130(33):10870-10871 (2008).

Caskey et al., "Selected Applications of Metal-Organic Frameworks in Sustainable Energy Technologies," Material Matters 4.4:111 (2009).

Centrone et al., "Raman Spectra of Hydrogen and Deuterium Adsorbed on a Metal-Organic Framework," Chem. Phys. Lett. 411:516-519 (2005).

Chae et al., "A Route to High Surface Area, Porosity and Inclusion of Large Molecules in Crystals," Nature 427, 523-527 (2004); Featured in (1) Chemical & Engineering News magazine, Feb. 9, 2004, (2) BBC World Service, Feb. 4, (3) New Scientist.

Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).

Chen et al., "High H2 Adsorption in a Microporous Metal-Organic Framework with Open-Metal Sites," Angew. Chem. Int. Ed. 44:4745-4749 (2005).

Chen et al., "A Microporous Metal-Organic Framework for Gas-Chomatographic Separation of Alkanes," Angew. Chem. Int. Ed. 45:1390-1393 (2006).

Choi et al., "Heterogeneity within Order in Crystals of a Porous Metal Organic Framework," J. Am. Chem. Soc. 133:11920-11923 (2011).

Cote et al., "Reticular Synthesis of Microporous and Mesoporous 2D Covalent Organic Frameworks," J. Am. Chem. Soc. 129:12914-12915 (2007).

Cui et al., "Iln Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).

Czaja et al., "Industrial applications of metal-organic frameworks," Chemical Society Reviews 38(5):1284-1293 (2009).

Deng et al., "Multiple Functional Groups of Varying Ratios in Metal-Organic Frameworks," Science 327:846-850 (2010).

Deng et al., "Robust dynamics" Nature Chem. 2:439-443 (2010).

Doonan et al., "Isoreticular Metalation of Metal-Organic Frameworks," J. Am. Chem. Soc. 131:9492-9493 (2009).

Doonan, C., "Hydrogen Storage in Metal-Organic Frameworks," Annual Merit Review Proceedings of DOE Hydrogen Program, May 22, 2009.

Doonan et al., "Exceptional ammonia uptake by a covalent organic framework," Nature Chem. 2:235-238 (2010).

Duren et al., "Design of New Materials for Methane Storage," Langmuir 20:2683-2689 (2004).

(56) References Cited

OTHER PUBLICATIONS

Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Galli et al., "Adsorption of Harmful Organic Vapors by Flexible Hydrophobic Bis-pyrazolate Based MOFs," Chem. Mater. 22(5):1664-1672 (2010).
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Han, SS et al., "Improved designs of metal-organic frameworks for hydrogen storage" Angew. Chem. Int. Ed. 2007, 46, pp. 6289-6292.
Han et al., "Covalent Organic Frameworks as Exceptional Hydrogen Storage Materials," J. Am. Chem. Soc. 130: 11580-11581 (2008).
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Holler et al., "The first dinitrile frameworks of the rare earth elements: [LnCl3(1,4-Ph(CN)2] and [Ln2Cl6(1,4Ph(CN) 2], Ln = Sm, Gd, Tb, Y; Access to novel metal-organic frameworks by solvent free synthesis in molten 1,4-benodinitril," Inorganic Chemistry 47(21): 10141-9 (2008).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: Apr. 6, 2010.
Howe, Patrick. International Search Report and Written Opinion for PCT/US2010/022777. Date of Mailing: Jun. 7, 2010.
Isaeva et al., "Metal-organic frameworks—new materials for hydrogen storage," Russian Journal of General Chemistry 77(4):721-739 (2007).
Kaderi et al., "Designed Synthesis of 3D Covalent Organic Frameworks," Science 316:268-272 (2007).

Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "A Metal-Organic Framework with a Hierarchical System of Pores and Tetrahedral Bbuilding Blocks," Angew. Chem. Int. Ed. 45:2528-2533 (2006).
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Uribe-Romo et al., "A Crystalline Imine-Linked 3-D Porous Covalent Organic Framework," J. Am. Chem. Soc. 131:4570-4571 (2009).
Vitillo et al., "Role of Exposed Metal Sites in Hydrogen Storage in MOFs," J. Am. Chem. Soc. 130(26):8386-8396 (2008).
Walton et al., "Understanding Inflections and Steps in Carbon Dioxide Adsorption Isotherms in Metal-Organic Frameworks," J. Am. Chem. Soc.130:406-407 (2008).
Wang et al., "Postsynthetic Covalent Modification of a Neutral Metal-Organic Framework," J. Am. Chem. Soc. 129 (41):12368-12369 (2007).
Wang et al., "Tandem Modification of Metal-Organic Frameworks by a Postsynthetic Approach," Angew. Chem. Int. 47:4699-4702 (2008).
Wang et al., "Colossal Cages in Zeolitic Imidazolate Frameworks as Selective Carbon Dioxide Reservoirs," Nature 453:207-211 (2008).
Wong-Foy, AG et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Hydrothermal Synthesis of a Metal-Organic Framework Containing Large Rectangular Channels," J. Am. Chem. Soc., 1995, 117, 10401-10402.
Yaghi et al., "Selective Guest Binding by Tailored Channels in a 3-D Porous Zinc(II)-1,3,5-Benzenetricarboxylate Network," J. Am. Chem. Soc., 119, 2861-2868 (1997).
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthetic Strategies, Structure Patterns, and Emerging Properties in the Chemistry of Modular Porous Solids," Acc. Chem. Res. 31:474-484 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi, Omar., "Porous Crystals For Carbon Dioxide Storage," slide presentation at the Fifth Annual Conference on Carbon Capture &

(56) References Cited

OTHER PUBLICATIONS

Sequestration, US Department of Energy on May 10, 2006 http://www.netl.doe.gov/publications/proceedings/06/carbon-seq/Tech°20Session°20193.pdf.

Yaghi et al., "Metal-Organic Frameworks: A Tale of Two Entanglements," Nature materials 6:92-93 (2007).

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Reticular Chemistry and Metal-Organic Frameworks for Clean Energy," MRS Bulletin 34:682-690 (2009).

Young, Lee W., International Search Report and Written Opinion, Date of Mailing of Report: May 7, 2008, International Application No. PCT/US08/51859.

Young, Lee W., "International search Report and Written Opinion," PCT/US08/06008, United States Patent & Trademark Office, Aug. 20, 2008.

Young, Lee W., International Search Report and Written Opinion, Date of Mailing: Dec. 2, 2008, International Application Number: PCT/US08/77741.

Young, Lee W., International Search Report and Written Opinion, Date of Mailing: Jan. 12, 2009, International Application Number: PCT/US08/70149.

Young, Jung Doo. International Search Report for PCT/US2010/050170. Date of Mailing: Jun. 8, 2011.

Zhao, Wei. The First Office Action for Chinese Application No. 200880003157.2. The State Intellectual Property Office of the People's Republic of China. Issue Date: Aug 5, 2011.

Kim, Su Mi, International Search Report and Written Opinion, Date of Mailing: Feb. 24, 2010, International Application Number: PCT/US09/46463.

Kim, Su Mi, International Search Report and Written Opinion for PCT/US2009/068731. Date of Mailing: Aug. 19, 2010.

Kim, Su Mi. International Search Report for PCT/US2010/039154. Date of Mailing: Feb. 23, 2011.

Klaes, Daphne. International Search Report and Written Opinion for PCT/US2010/021201. Date of Mailing: Apr. 27, 2010.

Kyoungmoo et al., "A Crystalline Mesoporous Coordination Copolymer with High Microporosity," Angew. Chem. Int. Ed. 47(4):677-680 (2008).

Lee, Ji Min. International Search Report for PCT/US2010/039284. Date of Mailing: Feb. 22, 2011.

Li et al., "Coordinatively Unsaturated Metal Centers in the Extended Porous Framewokr of Zn3(BDC)3-6CH3OH (BDC= 1,4-Benzenedicarboxylate)," J. Am. Chem. Soc. 2186-2187 (1998).

Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).

Li et al., "Design and Synthesis of an Exceptionally Stable and Highly Porous Metal-Organic Framework," 402:276-279 (1999); Featured in (1) Chemical and Engineering News (Nov. 22, 19999) and (2) Science News (Nov. 20, 1999).

Li et al., "A metal-organic framework replete with ordered donor-acceptor catenanes," Chem. Commun. 46:380-382 (2010).

Linder, Nora. International Preliminary Report on Patentability for PCT/US2010/022777. Date of Mailing: Aug. 11, 2011.

Long et al., "The Pervasive Chemistry of Metal-Organic Frameworks," Chem. Soc. Rev. 38:1213-1214 (2009).

Lu et al., "Synthesis and Structure of Chemically Stable Metal-Organic Polyhedra," J. Am. Chem. Soc. 131:(35) 12532-12533 (2009).

Mendoza-Cortes et al., "Adsorption Mechanism and Uptake of Methane in Covalent Organic Frameworks: Theory and Experiment," J. Phys. Chem. 114:10824-10833 (2010).

Michalitsch, Richard. International Search Report and Written Opinion for PCT/US2009/069700. Date of Mailing: May 7, 2010.

Millward et al., "Metal-Organic Frameworks with Exceptionally High Capacity for Storage of Carbon Dioxide at Room Temperature," J. Am. Chem. Soc. 127:17998-17999 (2005).

Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).

Morris et al., "Postsynthetic Modification of a Metal-Organic Framework for Stabilization of a Hemiaminal and Ammonia Uptake," Inorg. Chem. 50:6853-6855 (2011).

Moyse, Ellen, International Preliminary Report on Patentability and Written Opinion, Date of Issuance of Report: Nov. 17, 2009, International Application No: PCT/US08/006008.

Mulhausen, Dorothee. International Preliminary Report on Patentability for PCT/US2009/069700. Date of Mailing: Jul. 7, 2011.

Mulhausen, Dorothee. International Preliminary Report on Patentability for PCT/US2010/021201. Date of Mailing Jul. 28, 2011.

Natarajan et al., "Non-carboxylate based metal-organic frameworks (MOFs) and related aspects," Current Opinion in Solid State and Materials Science 13(3-4):46-53 (2009).

Ni et al,. "Porous Metal-Organic Truncated Octahedron Constructed from Paddle-Wheel Squares and Terthiophene Links," J. Am. Chem. Soc. 127:12752-12753 (2005).

Nickitas-Etienne, Athina, International Preliminary Report on Patentability and Written Opinion, Date of Issuance of Report: Jan. 19, 2010, International Application No: PCT/US08/70149.

Nickitas-Etienne, Athina. International Preliminary Report on Patentability for PCT/US2008/07741. Date of issuance of this report: Mar. 30, 2010.

Nickitas-Etienne, Athina, International Preliminary Report on Patentability for PCT/US2009/068731. Date of Issuance of the Report: Jun. 21, 2011.

Nickitas-Etienne, Athina. International Preliminary Report on Patentability for PCT/US2009/068849. Date of Mailing: Jun. 30, 2011.

Oisaki et al., "A Metal-Organic Framework with Covalently Bound Organometallic Complexes," J. Am. Chem. Soc. 132:9262-9264 (2010).

O'Keefe et al., "Frameworks for Extended Solids: Geometrical Design Principles," J. Solid State Chem. 152:3-20 (2000).

Okeeffe et al., "Reticular Chemistry—Present and Future Prospects—Introduction," J. Solid State Chem.178:V-VI (2005).

O'Keeffe et al., "The Reticular Chemistry Structure Resource (RCSR) Database of, and Symbols for, Crystal Nets," Am. Chem. Res. 41:1782-1789 (2008).

Park, Jae Woo. International Search Report for PCT/US2010/039123. Date of Mailing: Feb. 24, 2011.

Patteux, Claudine. International Search Report for PCT/US2010/043373. Date of Mailing: Oct. 10, 2010.

Peterson et al., "Ammonia Vapor Removal by Cu3(BTC)2 and Its Characterization by MAS NMR," J. Phys. Chem. C. 113(32):13906-13917 (2009).

Phan et al., "Synthesis, Structure, and Carbon Dioxide Capture Properties of Zeolitic Imidazolate Frameworks," Acc. Chem. Res 43:58-67 (2009).

Reineke et al., "From Condensed Lanthanide Coordination Solids to Microporous Frameworks Having Accessible Metal Sites," J. Am. Chem. Soc 121:1651-1657 (1999).

Reineke et al., "A Microporosity of Lanthanide-Organic Frameworks," Angew. Chem. Int. Ed. 38:2590-2594 (1999).

Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).

Rosi et al., "Advances in the Chemistry of Metal-Organic Frameworks," CrystEngComm 4:401-404 (2002).

Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.

Rosi et al., "Rod-Packings and Metal-Organic Frameworks Constructed from Rod-Shaped Secondary Building Units," J. Am. Chem. Soc. 127:1504-1518 (2005).

Rowsell et al., "Hydrogen Sorption in Functionalized Metal-Organic Frameworks," J. Am. Chem. Soc.126: 5666-5667 (2004).

(56) References Cited

OTHER PUBLICATIONS

Rowsell et al., "Metal-Organic Frameworks: A New Class of Porous Materials," Microporous Mesoporous Mater. 73:3-14 (2004).

Rowsell et al., "Strategies for Hydrogen Storage in Metal-Organic Frameworks," Angew. Chem. Int. Ed. 44: 4670-4679 (2005).

Rowsell et al., "Gas Adsorption Sites in a Large-Pore Metal-Organic Framework," Science 309:1350-1354 (2005).

Rowsell et al., "Characterization of H2 Binding sites in prototypical metal-organic frameworks by inelastic neutron scattering," J. Am. Chem. Soc. 127:14904-14910 (2005).

Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).

Siberio-Perez, "Raman Spectroscopic Investigation of CH4 and N2 Adsorption in Metal-Organic Frameworks," Chem. Mater. 19:3681-3685 (2007).

Sigma-Aldrich, Basolite C300 (MOF-199), catalog No. 688614; http://www.sigmaaldrich.com/catalog/ProductDetail.do?D7=0 &N5=SEARCH_CONCAT_PNO%7CBRAND_KEY &N4=688614%7CALDRICH&N25=0&QS=ON&F=SPEC.

Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.

\* cited by examiner

REVERSIBLE ETHYLENE OXIDE CAPTURE IN POROUS FRAMEWORKS

CROSS REFERENCE TO RELATED APPLICATIONS

This application is a U.S. National Stage Application filed under 35 U.S.C. §371 and claims priority to International Application No. PCT/US10/22777, filed Feb. 1, 2010, which application claims priority under 35 U.S.C. §119 to U.S. Provisional Application Ser. No. 61/149,069, filed Feb. 2, 2009, the disclosures of which are incorporated herein by reference in their entirety.

STATEMENT REGARDING FEDERALLY SPONSORED RESEARCH

The invention was funded in part by Grant No. W911NF-06-1-0405 awarded by the United States Army, Joint Science and Technology Office. The government has certain rights in the invention.

The subject matter of this application arises in part from a joint research agreement between the Regents of the University of California and BASF SE.

FIELD OF THE INVENTION

This disclosure relates to porous frameworks for ethylene oxide adsorption, separation and recovery.

BACKGROUND

Ethylene oxide is the chief precursor to ethylene glycol and other high volume chemicals as well as being used in sterilization procedures.

Ethylene oxide is produced by oxidation of ethylene with oxygen, typically using a modified silver catalyst at 200-300° C. Often chemical modifiers such as chlorine are also included. Pressures used are in the region of 1-2 MPa. The typical yield for this reaction under industrial conditions is 70-80%. Approximately 15,000,000,000 kg are produced annually.

Most ethylene oxide is consumed as the precursor to ethylene glycol as well as a variety of other chemicals. Ethylene glycol is more commonly known for its use as an automotive coolant and antifreeze. Other chemical applications include the production of ethanolamine, diverse surfactants, and glycol ethers such as ethoxyethanol. Ethylene oxide is a highly reactive chemical due to the ease of opening of its highly strained three-membered ring, the bond being weaker than ether and the molecule less stable.

SUMMARY

The porous materials of the disclosure are useful for ethylene oxide separation and recovery.

The disclosure provides methods and compositions useful for separation of ethylene oxide from a mixture of gases via interaction of ethylene oxide with a reactive functionality in a porous metal-organic framework, covalent-organic framework, zeolitic-imidazolate framework, or related material. The reactive functionality is developed such that ethylene oxide reversibly, and without a ring-opening reaction, adsorbs to the porous framework structure. The compositions of the disclosure can be used in a traditional adsorption separation, including any pressure-swing adsorption, temperature-swing adsorption, or combination of the two, as well as membrane-based or flow-through type adsorption.

The disclosure provides a method of separating ethylene oxide in a fluid or gas mixture comprising contacting a porous framework with the fluid or gas mixture, wherein the ethylene oxide is absorbed or adsorbed to the porous metal organic framework and wherein the porous framework comprises coordinatively unsaturated metal sites or an amino functionality providing a reactive group capable of undergoing reaction to form a covalent, hydrogen, ionic or other bond with ethylene oxide. In one embodiment, the method comprises a replaceable guest species within the porous framework. In yet another embodiment, the porous framework comprises an iso-reticular metal organic framework. In yet a further embodiment, the metal in said framework is unsaturated. In one embodiment, the reactive group comprises a reactive Lewis acid group. In yet another embodiment, the porous framework comprises a plurality of unsaturated metals linked by a trimesate linking moiety. In a further embodiment, the porous metal organic framework comprises MOF-199.

The disclosure also provides a porous framework for separation of ethylene oxide comprising coordinatively unsaturated metal sites or an amino functionality providing a reactive group capable of undergoing reaction to form a covalent, hydrogen, ionic or other bond with ethylene oxide. In one embodiment, the framework comprises a replaceable guest species within the porous framework. In yet another embodiment, the porous framework comprises an iso-reticular metal organic framework. In yet another embodiment, the metal in said framework is unsaturated. In one embodiment, the reactive group comprises a reactive Lewis acid group. In yet another embodiment, the framework comprises a plurality of unsaturated metals linked by a trimesate linking moiety. In a further embodiment, the porous metal organic framework comprises MOF-199.

The disclosure also provides a device comprising a porous framework as described above for separating ethylene oxide from a mixed gas or fluid mixture. In one embodiment, the device comprises a fixed bed of adsorbent material.

The disclosure also provides a method of separating ethylene oxide in a mixed fluid or gas comprising contacting a device of the disclosure with the mixed fluid or gas, wherein the ethylene oxide is absorbed or adsorbed to the porous framework thereby separating the ethylene oxide from the mixed fluid or gas.

The disclosure also provides a filter medium for purifying ethylene oxide comprising a porous framework as described above. In yet another embodiment, the disclosure provides a filter system comprising said filter medium.

The disclosure also provides a filtration system comprising a gas or fluid inlet and an outlet; a metal organic framework (MOF), iso-reticular metal organic framework (IRMOF) or a combination thereof disposed between the inlet and the outlet, wherein the MOF or IRMOF has been functionalized to bind ethylene oxide, wherein a fluid or gas comprising ethylene oxide enters the inlet and contacts the MOF or IRMOF as it flows towards the outlet, and wherein the fluid or gas is substantially depleted of ethylene oxide at the outlet. In one embodiment, the system comprises a fixed bed system. In another embodiment, the fluid flow is a linear flow. In yet another embodiment, the system comprises a pressure swing adsorption system. In yet another embodiment, the system comprises a temperature swing adsorption system.

DETAILED DESCRIPTION

Figure 1:
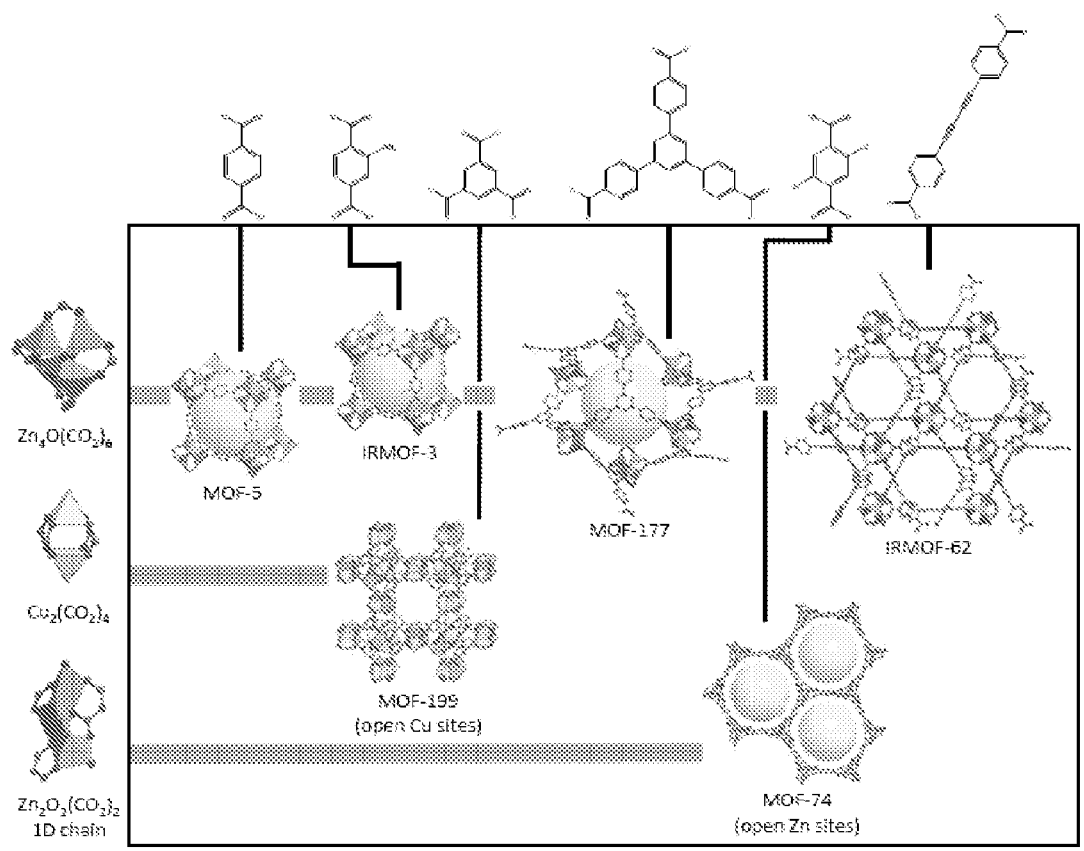
FIG. 1 shows single crystal x-ray structures of the benchmark MOFs: The $Zn_4O(CO_2)_6$ cluster linked by terephthalate (MOF-5), 2-aminoterephthalate (IRMOF-3), benzene-1,3,5-tris(4-benzoate) (MOF-177), and diacetylene-1,4-bis-(4-benzoic acid) (IRMOF-62); the $Cu_2(CO_2)_4$ cluster linked by trimesate (MOF-199); and 1D $Zn_2O_2(CO_2)_2$ chains linked by 2,5-dihydroxyterephthalate (MOF-74). C, O, N are represented and metal ions as polyhedra. H atoms are omitted for clarity. See Table 1 for further structural information.

As used herein and in the appended claims, the singular forms "a," "and," and "the" include plural referents unless the context clearly dictates otherwise. Thus, for example, reference to "a species" includes a plurality of such species and reference to "the framework" includes reference to one or more frameworks and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed Methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Ethylene oxide is the chief precursor to ethylene glycol and other high volume chemicals as well as being used in sterilization procedures. Approximately 15,000,000,000 kgs are produced annually.

Ethylene oxide is a highly reactive chemical due to the ease of opening of its highly strained three-membered ring, the bond being weaker than ether and the molecule less stable. Thus, when being separated or recovered from a mixture the ability to eliminate or reduce the ring opening is important to improve yield and production.

Zeolite type materials adsorb ethylene oxide, but cause a ring-opening reaction and are therefore not reversible. Activated carbon type materials are unable to adsorb ethylene oxide in any appreciable amount. The disclosure demonstrates that MOFs including IRMOFs can adsorb ethylene oxide without causing ring-opening thus providing useful materials for separating ethylene oxide from carrier gases and liquids.

A fluid or gas mixture refers to a multi-component fluid or gas. An ethylene oxide gas or fluid mixture refers to a gas or fluid mixture comprising ethylene oxide. A substantially purified ethylene oxide gas or fluid mixture refers to a gas or fluid mixture wherein the percent composition of ethylene oxide has been increased compared to a starting mixture.

The disclosure provides methods, compositions an devices/systems for separation or recovery of ethylene oxide from a carrier gas or fluid or other contaminants following synthesis. The disclosure utilizes microporous framework materials comprising coordinatively unsaturated metal sites, reactive side groups or a combination thereof, wherein the microporous materials adsorb ethylene oxide without cracking the ring structure. The microporous material can comprise a metal organic framework (MOF), an isoreticulated metal organic framework (IRMOF), a covalent organic framework (COF), a zeolitic imidozolate framework (ZIF) or a combination thereof. In one embodiment, a MOF or IRMOF comprises a reactive side group that can bond (either covalently, ionically or through hydrogen bonds) with an analyte such as ethylene oxide. Devices comprising a MOF or IRMOF of the disclosure can be used to separate ethylene oxide in a multi-component gas or fluid. The compositions and methods can be used in combination with other gas removal compositions and devices including, for example, activated charcoal and the like to further improve recover by either bonding to ethylene oxide or by further removal of a contaminating gas or carrier gas.

Microporous frameworks useful in the methods, compositions and devices of the disclosure include metal-organic-frameworks. Metal-organic frameworks (MOFs) are a class of crystalline porous materials whose structure is composed of metal-oxide units joined by organic linkers through covalent bonds. These metal oxides and linkder can be further functionalized with groups that promote selective adsorption of a desired analyte. The flexibility with which these components can be varied has led to an extensive class of MOF structures with ultra-high surface areas, far exceeding those achieved for porous carbons. MOFs exhibit high thermal stability, with decomposition between 350° C. and 400° C. in the case of MOF-5 (Eddaoudi M, et al., Science 295:469-472, 2002), ensuring their applicability across a wide temperature range. The unprecedented surface area and the control with which their pore metrics and functionality can be designed provides limitless potential for their structure to be tailored to carry out a specific application, thus being superior to activated carbons in many applications. Table 1 give some characteristics of various MOFs that can be generated using techniques described herein.

TABLE 1

Diverse characteristics of the benchmark MOFs

| MOF | SBU* 0D | SBU* 1D | Open metal sites† | Functionalized pore‡ | Catenated§ | Ultrahigh surface area | Surface area, $m^2/g$¶ | Pore volume, $cm^3/g$ |
|---|---|---|---|---|---|---|---|---|
| MOF-5 | ■ | | | | | ■ | 2,205 | 1.22 |
| IRMOF-3 | ■ | | | ■ | | | 1,568 | 1.07 |
| MOF-74 | | ■ | ■ | | | | 632 | 0.39 |
| MOF-177 | ■ | | | | | ■ | 3,875 | 1.59 |
| MOF-199 | ■ | | ■ | | | | 1,264 | 0.75 |
| IRMOF-62 | ■ | | | ■ | ■ | | 1,814 | 0.99 |

*Secondary building units (SBUs) are either discreet inorganic clusters (0D) or linear chains (1D).
†MOF-74 contains pyramidal 5-coordinate zinc, and MOF-199 contains square 4-coordinate copper.
‡IRMOF-3 contains amino functionality, and IRMOF-62 contains alkyne functionality.
§IRMOF-62 is quadruply interpenetrated.
¶Surface areas calculated by the BET method for samples used in this study. These may differ from reported values as a result of variation in handling and activation procedures.

While application of MOFs to high-density gas storage has been studied, virtually no work has been undertaken to measure their capacity for ethylene oxide adsorption properties. Equilibrium adsorption does not adequately predict selectivity, as dynamic capacity is influenced strongly by the kinetics of adsorption. The kinetic properties of adsorption in MOFs are largely unexamined.

The disclosure demonstrates the viability of functionalizing the organic links of porous metal-organic frameworks to generate functionalized frameworks comprising reactive groups. Such reactive groups are useful in the removal (e.g., absorption or adsorption) of gas contaminates during ethylene oxide recovery or in the adsorption of ethylene oxide in a fluid or gas environment. Organic frameworks of the disclosure have the general structure M-L-M, wherein L is a linking moiety and M are transition metals.

As used herein, a "core" refers to a repeating unit or units found in a framework. Such a framework can comprise a homogenous repeating core or a heterogeneous repeating core structure. A core comprises a transition metal or cluster of transitions metals and a linking moiety. A plurality of cores linked together defines a framework.

The term "cluster" refers to identifiable associations of 2 or more atoms. Such associations are typically established by some type of bond—ionic, covalent, Van der Waals, and the like.

A "linking cluster" refers to a one or more reactive species capable of condensation comprising an atom capable of forming a bond between a linking moiety and a metal group or between a linking moiety and another linking moiety. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings.

A "linking moiety" refers to a mono-dentate or polydentate compound that bind a transition metal or a plurality of transition metals, respectively. Generally a linking moiety comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster (e.g., a multidentate function groups) may be covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached. It is understood that the ligands possessing multidentate functional groups bring with them corresponding counter cations, such as $H^+$, $Na^+$, $K^+$, $Mg_2^+$, $Ca_2^+$, $Sr_2^+$, ammonium ion, alkylsubstituted ammonium ions, and arylsubstituted ammonium ions, or counter anions, such as $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^-$, $SO_3^-$, $PO_3^-$, $CO_3^-$, $PF_6^-$ and organic counter ions such as acetate $CH_3CO_2^-$, triphlates $CF_3SO_3^-$.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one embodiment, the linking moiety is selected from any of the following:

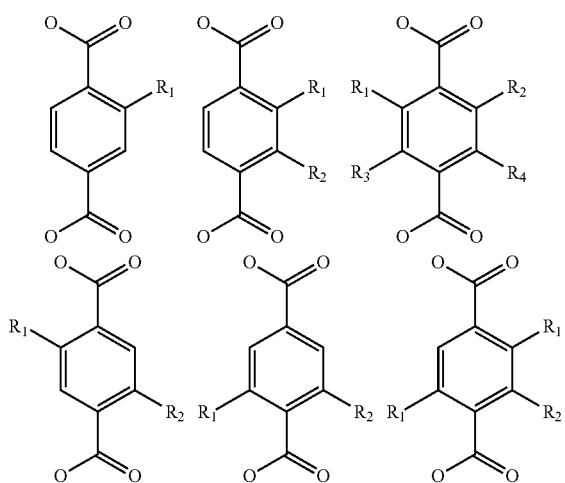

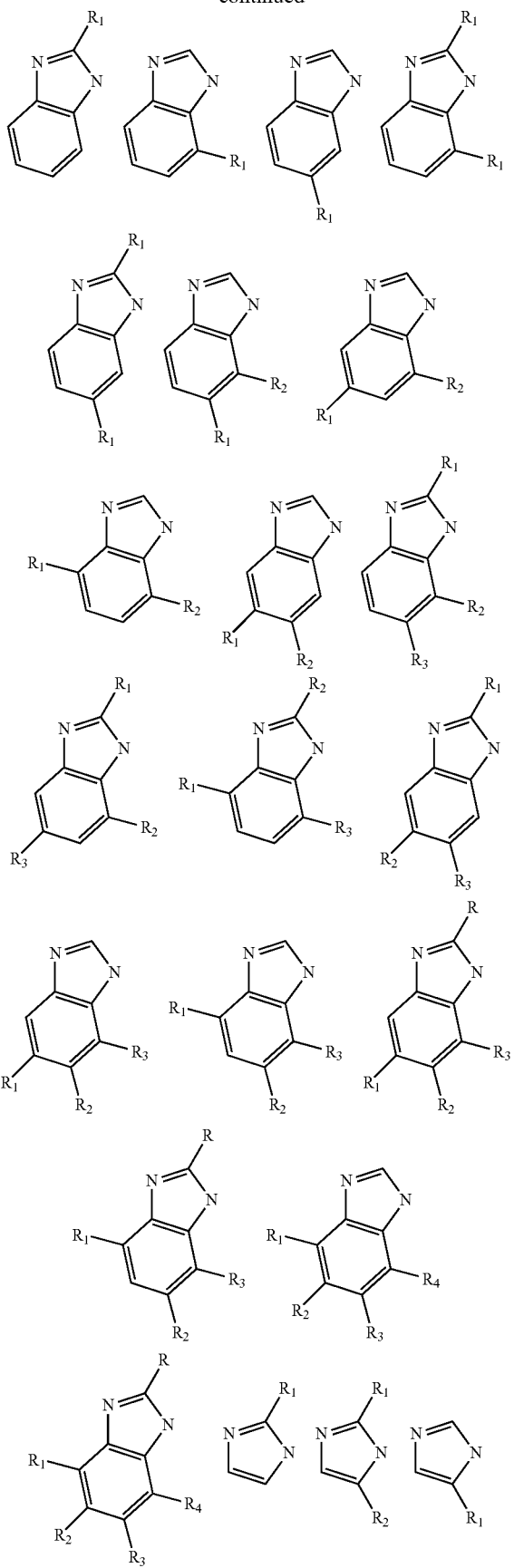

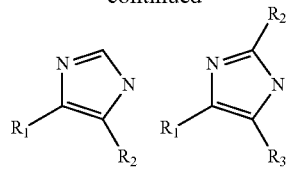

wherein $R_1, R_2, R_3, R_4 = NH_2$, CN, OH, $=O$, $=S$, SH, P, Br, CL, I, F,

wherein X=1, 2, or 3.

An isoreticular metal-organic framework (IRMOF) according to the disclosure comprises a plurality of secondary building units (SBUs), each of the plurality of SBUs comprising an $M_4O(CO_2)_6$ cluster. A linking moiety links adjacent SBUs, the linking moiety comprising a linear ditopic carboxylate having at least one phenyl group and at least one functional group X attached to at least one phenyl group. The IRMOF formed has substantial permanent porosity and is very stable, with or without the presence of guest molecules. M in the SBU is a metal cation. For example, the metal cation can be selected from the group consisting of a beryllium, zinc, cadmium, mercury, and any of the transition metals (in the periodic table, scandium through copper, yttrium through silver, lanthanum through gold, and all known elements from actinium on). X may be any suitable functional group as necessary and/or desired.

A method of forming an isoreticular metal-organic framework (IRMOF) comprises the step of dissolving at least one metal salt and at least one linear ditopic carboxylate in a solvent to form a solution. The solvent may be any suitable solvent such as, for example, any nitrogen containing solvent having a boiling point of less than about 250° C. The solution is then crystallized to form the targeted IRMOF.

In one embodiment, the linear ditopic carboxylate/carboxylic acid has at least one phenyl group. In another embodiment, at least one functional group X is attached to the at least one phenyl group.

The crystallizing step is carried out by leaving the solution at room temperature; adding a diluted base to the solution to initiate the crystallization; diffusing a diluted base into the solution to initiate the crystallization; and/or transferring the solution to a closed vessel and heating to a predetermined temperature.

Metal-organic microporous solids have been prepared using a metal ion that provides tetrahedral coordination, zinc (II), in the presence of the ditopic ligand. Stable MOF and IRMOFs can be made using metal ions from the following list: $Mg_2^+, Ca_2^+, Sr_2^+, Ba_2^+, Sc_3^+, Y_3^+, Ti_4^+, Zr_4^+, Hf_4^+, V_4^+, V_3^+, V_2^+, Nb_3^+, Ta_3^+, Cr_3^+, Mo_3^+, W_3^+, Mn_3^+, Mn_2^+, Re_3^+, Re_2^+, Fe_3^+, Fe_3^+, R_3^+, Ru_2^+, Os_3^+, Os_2^+, Co_3^+, Co_2^+, Rh_2^+, Rh^+, Ir_2^+, Ir^+, Ni_2^+, Ni^+, Pd_2^+, Pd^+, Pt_2^+, Pt^+, Cu_2^+, Cu^+, Ag^+, Au^+, Zn_2^+, Cd_2^+, Hg_2^+, Al_3^+, Ga_3^+, In_3^+, Tl_3^+, Si_4^+, Si_2^+,$ $Ge_4^+$, $Ge_2^+$, $Sn_4^+$, $Sn_2^+$, $Pb_4^+$, $Pb_2^+$, $As^{5+}$, $As_3^+$, $As^+$, $Sb^{5+}$, $Sb_3^+$, $Sb^+$, and $Bi^{5+}$, $Bi_3^+$, $Bi^+$; along with the corresponding metal salt counteranion.

The preparation of the microporous materials of this disclosure can be carried out in either an aqueous or non-aqueous system. The solvent may be polar or nonpolar as the case may be. The solvent may be the required templating agent, or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n⁻propanol, isopropanol, acetone, 1,2-dichloroethane, methylene chloride, chloroform, carbon tetrachloride, tetrahydrofuran, dimethylformamide, dimethylsulfoxide, N-methylpyrollidone, dimethylacetamide, diethylformamide, thiophene, pyridine, ethanolamine, triethylamine, ethylenediamine, and the like. Those skilled in the art will be readily able to determine an appropriate solvent based on the starting reactants. However, the choice of solvent is not believed to be critical in obtaining the microporous materials of this disclosure. Any templating agent known to affect the outcome of reaction can be used.

The crystallizing step is carried out by: leaving the solution at room temperature or in isothermal oven for up to 200° C.; adding a diluted base to the solution to initiate the crystallization; diffusing a diluted base into the solution to initiate the crystallization; and/or transferring the solution to a closed vessel and heating to a predetermined temperature.

Metal-organic frameworks including MOF-199 and MOF-74 have demonstrated surprisingly good capacity for ethylene oxide.

The disclosure demonstrates that coordinatively unsaturated metal sites (e.g., MOF-74 and MOF-199) and amino functionality (e.g., IRMOF-3) prove effective in adsorbing contaminants that interact strongly with those groups. For example, MOF-199 demonstrates efficacy equal to or greater than BPL-carbon against all gases and vapors tested except chlorine. It is particularly effective in removing gases that are vexing for activated carbons such as ammonia and ethylene oxide.

A successful MOF-based dynamic adsorption medium will contain some reactive functionality, often in the form of a coordinatively unsaturated metal site. A variety of MOFs with reactive functionality can be developed and there exists immense potential for the development of additional MOFs with untested functionalities and metals. Furthermore, the performance of any MOF can be improved using various techniques to design pores with reactive side-groups or impregnated with reactive ions and compounds.

Many applications involve capture of gaseous compounds from mixtures containing potentially reactive impurities or residual humidity. The effect of impurities present in a particular setting on both the structure of a MOF adsorbent and on the binding affinity of the target adsorbate can be addressed by including substructure with reactive side-groups tailored to bind a particular contaminant or the molecule of interest.

The disclosure provides a column filtration/separation column or fixed bed comprising a MOF, IRMOF or a combination thereof capable of separating ethylene oxides from other contaminating or carrier gases. Ethylene oxide, usually mixed at low percentage in some carrier gas, is flowed into a bed of, for example, MOF-199, MOF-74 and the like. The ethylene oxide gas is adsorbed with high capacity (greater than about 2%, 3%, 4%, 5% or more by weight) within, for example, MOF-199 while the carrier gas(es) are not appreciably adsorbed. Upon saturation, desorption of the ethylene oxide from the porous material can be effected in a number of ways, including lowering pressure, increasing temperature, and by flowing another carrier gas through the porous material. For example, a chamber(s) containing a porous organic framework of the disclosure (e.g., MOF-199) can be pressurized with a mixture of gases comprising ethylene oxide. Pressure will be dropped initially to collect all carrier gases, and then further to collect the purified ethylene oxide. Because desorption generally takes longer than adsorption, several containers can be used performing the same function, so that while one container is being pressurized, the others are desorbing the purified ethylene oxide.

The disclosure provides an apparatus and method for separating ethylene oxide from a multi-component gas comprising using a separation system (e.g., a fixed-bed system and the like) having a feed side and an effluent side separated by a MOF or IRMOF of the disclosure. The MOF or IRMOF may comprise a column separation format.

In one embodiment of the disclosure, an ethylene oxide separation material comprising a MOF or IRMOF is provided.

In one embodiment, a porous metal organic framework (e.g., MOF-199, MOF-74 or a combination thereof) is used to selectively bind ethylene oxides in a fluid or gas comprising a contaminant or carrier gas. The porous framework is capable of separating ethylene oxide from a mixture of gases via interaction of ethylene oxide with a reactive functionality in the porous metal-organic framework, covalent-organic framework, zeolitic-imidazolate framework, or related material. The reactive functionality adsorb ethylene oxide reversibly, and without a ring-opening reaction. Such separation can be performed in any number of separation systems such as, for example, any pressure-swing adsorption, temperature-swing adsorption, or combination of the two, as well as membrane-based or flow-through type adsorption.

In one embodiment, ethylene oxide, usually mixed at low percentage in some carrier gas, is flowed into a bed of MOF-199. The gas is adsorbed (e.g., at about 2%, 3%, 4%, 5% or more capacity) within MOF-199 while the carrier gas(es) are not appreciably adsorbed. Upon saturation, desorption of the ethylene oxide from the material can be effected in a number of ways, including lowering pressure, increasing temperature, and by flowing another carrier gas through the system.

In another embodiment, a pressure-swing adsorption setup is used to separate the ethylene oxide. Chambers containing MOF-199 will be pressurized with a mixture of gases including ethylene oxide. Pressure will be dropped initially to collect all carrier gases, and then further to collect the purified ethylene oxide. Because desorption generally takes longer than adsorption, the most likely implementation will include several containers performing the same function, so that while one container is being pressurized, the others are desorbing the purified ethylene oxide. The systems comprising a MOF-199, MOF-74 or combination thereof can be in series or parallel.

For example, MOF-199 binds the ethylene oxide, while the contaminant is removed. The MOF-199 binds the ethylene oxide while maintaining the ring structure (i.e., not "cracking" the ring"). The MOF-199 (or other porous organic framework) can be in a column device and the ethylene oxide containing gas or liquid is passed through the column. For example, the MOF-199 can be in a fixed bed device.

One such use of the MOFs and IRMOFs of the disclosure includes personal protection device. In this applications pertaining to personal protection depend on the irreversibility of adsorbate binding. The irreversible color change reported for some adsorbate/MOF pairings serves as evidence of irreversibility, which for protective applications is often desirable. However, for other applications such as gas storage, MOFs are known to bind guests reversibly.

As demonstrated below metal-organic frameworks including MOF-199 and MOF-74 have demonstrated surprisingly good capacity for ethylene oxide.

EXAMPLES

Preparation of MOFs.

MOFs were prepared and activated in bulk quantities using modified literature procedures, including those described herein. Each sample was characterized by powder X-ray (Cu Kα) diffraction (PXRD) and N2 adsorption isotherm. Apparent surface areas were determined by the Brunauer, Emmett, and Teller method (BET) and were commensurate with reported values. MOFs were stored under inert atmosphere.

MOF-5: $Zn_4O(C_9H_4O_4)_3$.

Terephthalic acid (3 g, $2\times10^{-2}$ mol) and $Zn(NO_3)_2.4H_2O$ (14 g, $5.4\times10^{-2}$ mol) were dissolved in 300 mL diethylformamide in a 500 mL jar with sonication. The jar was capped tightly at placed in a 100° C. oven for three days. The mother liquor was decanted and the large yellow crystalline product washed with diethylformamide and then HPLC grade (pentene stabilized) chloroform. The product was immersed in chloroform, which was decanted and replaced with fresh chloroform twice over three days. Product was evacuated to dryness and heated under vacuum to 120° C. for 17 hours. Sample was backfilled and stored under nitrogen. The BET surface area was measured to be 2205 $m^2/g$.

IRMOF-3: $Zn_4O(C_8H_5NO_4)_3$.

2-aminoterephthalic acid (5.96 g, $3.29\times10^{-2}$ mol) and $Zn(NO_3)_2.4H_2O$ (37.47 g, $1.43\times10^{-1}$ mol) were dissolved in 800 mL diethylformamide in a 1 L jar with wonication. The jar was capped tightly at placed in a 100° C. oven overnight (~15 hours). The mother liquor was decanted and the large brown crystalline product washed with diethylformamide and then HPLC grade (pentene stabilized) chloroform. The product was immersed in chloroform, which was decanted and replaced with fresh chloroform twice over three days. Product was evacuated to dryness and heated under vacuum to 120° C. for 23 hours. Sample was backfilled and stored under nitrogen. The BET surface area was measured to be 1568 $m^2/g$.

MOF-74: $Zn_2(C_8H_2O_6)$.

2,5-dihydroxyterephthalic acid (1.00 g, $5.05\times10^{-3}$ mol) and $Zn(NO_3)_2.4H_2O$ (4.50 g, $1.72\times10^{-2}$ mol) were dissolved in 100 mL dimethylformamide in a 400 mL jar with sonication. 5 mL water were added, followed by additional sonication. The jar was capped tightly and placed in a 110° C. oven for 20 hours. The mother liquor was decanted and the yellow crystalline product washed three times with dimethylformamide, then three times with methanol. The product was immersed in methanol, which was decanted and replaced with fresh methanol three times over four days. Product was evacuated to dryness and heated under vacuum to 150° C. over one hour, held at 150° C. for 10 hours, heated to 265° C. over one hour and held for 12 hours. Sample was backfilled and stored under nitrogen. The BET surface area of the sample was measured to be 632 $m^2/g$.

MOF-177: $Zn_4O(C_{27}H_{15}O_6)_2$.

Benzene-1,3,5-tris-(4-benzoic acid) (2.0 g, $4.6\times10^{-3}$ mol) and $Zn(NO_3)_2.4H_2O$ (7.2 g, $2.8\times10^{-2}$ mol) were dissolved in 200 mL diethylformamide in a 500 mL jar. The jar was capped tightly and placed in a 100° C. oven for 24 hours. The mother liquor was decanted and the colorless crystalline product washed with dimethylformamide and immersed in HPLC grade (pentene stabilized) chloroform, which was decanted and replaced with fresh chloroform three times over four days. Solvent was decanted from the product, which was placed in a Schlenk flask. The opening of the flask was cracked slightly to vacuum (just enough to see a pressure change on the Schlenk line) and left for 12 hours. It was then opened slightly more and left for 12 hours. It was then opened fully to vacuum and left for 24 hours at room temperature. Sample was backfilled and stored under nitrogen. The BET surface area of the sample was measured to be 3875 $m^2/g$.

MOF-199: $Cu_2(C_9H_3O_6)_{4/3}$.

Trimesic acid (5.00 g, $2.38\times10^{-2}$ mol) and $Cu(NO_3)_2.2.5H_2O$ (10.01 g, $4.457\times10^{-2}$ mol) were dissolved in 85 mL dimethylformamide in a 400 mL jar by sonication. 85 mL ethanol were added, followed by sonication. 85 mL water were added, followed by sonication. The jar was capped tightly and placed in a 85° C. oven for 24 hours. Sky blue powdered product was filtered, washed with dimethylformamide and ethanol, and immersed in dichloromethane, which was decanted and replaced with fresh dichloromethane three times over four days. Product was evacuated to dryness and heated under vacuum to 170° C. until color was deep purple (~2 days). Sample was backfilled and stored under nitrogen. The BET surface area of the sample was measured to be 1264 $m^2/g$.

IRMOF-62: $Zn_4O(C_{18}H_8O_4)_3$.

Diacetylene-1,4-bis-(4-benzoic acid) (20.28 g, $6.986\times10^{-2}$ mol) and $Zn(CH_3CO_2)_2.2H_2O$ (30.35 g, $1.383\times10^{-1}$ mol) were stirred in 1.5 L dimethylformamide at room temperature for 10 hours. Off-white powdered product was filtered, washed with dimethylformamide, dichloromethane, and immersed in dichloromethane. The product was filtered, washed with dichloromethane, and immersed in dichloromethane daily for three days. Product was evacuated at room temperature for 18 hours, then at 150° C. for 27 hours. Sample was backfilled and stored under nitrogen. The BET surface area of the sample was measured to be 1814 $m^2/g$.

Breakthrough Testing.

A schematic representation of the breakthrough test systems is described herein. Gasses were purchased from Lehner and Martin, Inc, Airgas, and Scott-Marrin, Inc. as certified mixtures in a balance of $N_2$, $Cl_2$ at 4%, CO at 1.05%, $SO_2$ at 1.00% and $NH_3$ at 0.99%. Flow rate was monitored using a Gilmont rotameter and held at 25 mL/min. Experiments were carried out with the adsorbent at room temperature (25° C.). Detection of the effluent gas from the sample was performed using a Hiden Analytical HPR20 mass spectrometer. Concentrations of $N_2$, $O_2$, and the contaminant gas were sampled continuously at a minimum rate of 3 points per minute. The concentration of the contaminant gas was calibrated by comparing to the concentration recorded by the mass spectrometer under unimpeded flow of the source mixture.

Liquid vapors were generated in a balance of nitrogen by a Vici Metronics, Inc. Dynacalibrator model 230 vapor generator, capable of delivering a vapor concentration with ±2% precision. A constant flow rate of 79 mL/min was generated by the vapor generator. The gasses generated for the experiments were mixtures in nitrogen of 64 ppm THT, 1240 ppm EtO, 440 ppm benzene, and 380 ppm methylene chloride. Experiments were carried out with the adsorbent at 25° C. Detection of the effluent gas from the sample was performed using a Thermo-Fisher Antaris IGS Fourier-transform infrared spectrometer. The spectrometer was calibrated for detection of each contaminant vapor using the TQAnalyst software package with a minimum of 16 calibration points across the operating detection range. The concentration of the contaminant vapor was sampled continuously at a minimum rate of 3 points per minute.

All experiments were carried out using a fritted 1.6 cm inner diameter glass sample tube. A bed of MOF 1.0 cm in height (0.4 cm in the case of tetrahydrothiophene tests) was deposited onto the glass frit under inert atmosphere. All samples were purged with ultra-high purity N2 gas for 20 minutes prior to testing. Testing was carried out with sample cell at room temperature (25° C.).

Dynamic Adsorption Capacity.

In each experiment, the "breakthrough concentration" for each contaminant is defined as 5% of the feed concentration. The time at which the concentration of contaminant gas in the effluent surpasses the breakthrough concentration is designated as the "breakthrough time." The dynamic adsorption capacity is calculated in each case by dividing the total mass of gas adsorbed prior to breakthrough by the mass of adsorbent.

Capture of Gaseous Contaminants.

Figure 2:
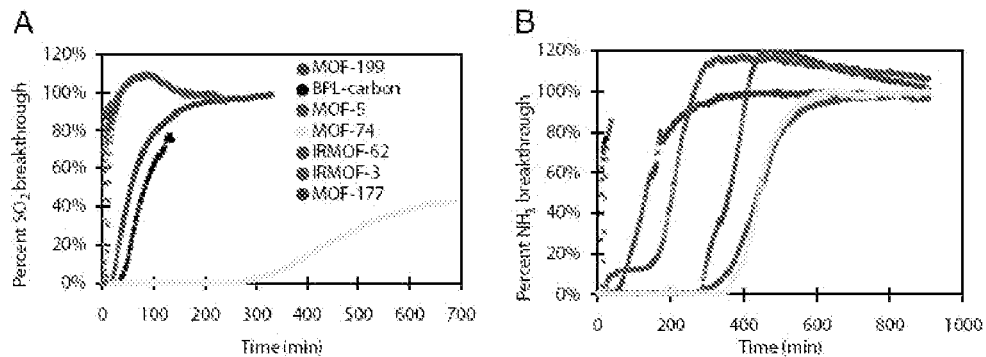
FIG. 2 shows selected kinetic breakthrough curves of gaseous (a) $SO_2$ and (b) $NH_3$ contaminants in the benchmark MOFs.

Breakthrough curves for $SO_2$, $NH_3$, $Cl_2$, and CO adsorption in MOF-5, IRMOF-3, IRMOF-62, MOF-74, MOF-177, MOF-199 (the benchmark MOFs), and BPL-carbon were recorded. Selected plots of breakthrough curves and estimated dynamic adsorption capacities for gaseous contaminants are presented in FIG. 2 and Table 2, respectively. No significant retention of CO was observed for any of the materials. Carbon monoxide breakthrough curves do not differ from that measured for a blank sample cell and have been omitted for clarity.

in that case, BPL-carbon is the more successful adsorbent. Despite their high capacities for thermodynamic gas adsorption, it is clear that MOFs lacking reactive adsorption sites are ineffective in kinetic gas adsorption.

Coordinatively unsaturated metal sites are known to be reactive as Lewis acids. They demonstrate efficacy as adsorption sites in testing of MOF-199 and MOF-74. MOF-199, which contains an open copper(II) site, outperforms BPL-carbon by a factor of 59 in ammonia adsorption and performs equally well in adsorbing sulfur dioxide. MOF-74 is even more effective, adsorbing more than 62 times the amount of ammonia and nearly 6 times the amount of sulfur dioxide as the activated carbon sample. In both cases, the highly reactive 5-coordinate zinc species in MOF-74 as well as the potentially reactive oxo group, may contribute to the highly successful kinetic adsorption. MOF-199 is less successful when challenged with $Cl_2$ due to the fact that $Cl_2$ does not typically act as a ligand. However, MOFs with open metal sites tend to be Lewis acidic and therefore highly effective as adsorption media for gases that can act as Lewis bases, which is a weakness in activated carbons.

While open metal sites are reactive electron deficient groups, amines constitute a common reactive electron rich group that is available for hydrogen bonding as well. As noted above, the presence of the amine in IRMOF-3 affords a vast improvement relative to MOF-5 in adsorption of $NH_3$, a molecule that readily forms hydrogen bonds. Relative to BPL-carbon, IRMOF-3 adsorbs almost 71 times as much ammonia before breakthrough. Furthermore, IRMOF-3 is observed to outperform BPL-carbon by a factor of 1.76 in adsorption of

TABLE 2

Dynamic adsorption capacities of the benchmark MOFs for gaseous contaminants measured in grams of gas per gram of adsorbent

| Gas | MOF-5 | IRMOF-3 | MOF-74 | MOF-177 | MOF-199 | IRMOF-62 | BPL carbon | Improvement factor * |
|---|---|---|---|---|---|---|---|---|
| Sulfur dioxide | 0.001 | 0.006 | 0.194 † | <0.001 | 0.032 | <0.001 | 0.033 | 5.88 |
| Ammonia | 0.006 | 0.105 † | 0.093 | 0.042 | 0.087 | 0.023 | 0.001 | 105 |
| Chlorine | ‡ | 0.335 † | ‡ | <0.001 | 0.036 | 0.092 | 0.190 | 1.76 |
| Tetrahydrothiophene | 0.001 | 0.007 | 0.090 | <0.001 | 0.351 † | 0.084 | 0.123 | 2.85 |
| Benzene | 0.002 | 0.056 | 0.096 | 0.001 | 0.176 † | 0.109 | 0.155 | 1.14 |
| Dichloromethane | <0.001 | 0.001 | 0.032 | <0.001 | 0.055 † | 0.019 | 0.053 | 1.04 |
| Ethylene oxide | 0.001 | 0.002 | 0.110 | <0.001 | 0.095 † | 0.011 | 0.010 | 9.50 |

* Expresses the ratio of dynamic adsorption capacity of the best-performing MOF (†) to that of BPL carbon.
† Best-performing MOFs.
‡ Experiments were not performed because of corrosion of the apparatus by chlorine.

Retention of ammonia in all the benchmark MOFs to was a vast improvement relative to BPL-carbon, three of the MOFs (IRMOF-3, MOF-74, MOF-199) attaining at least 59-fold improvement in dynamic adsorption capacity. However, for the other gases tested MOF-5 and MOF-177 exhibit worse dynamic capacity than BPL-carbon despite having higher surface area than all other materials tested. The lack of reactive functionality paired with the open, highly connected pore structure is therefore thought to make for an ineffective dynamic adsorption medium. Indeed, simply adding an amino functionality to the MOF-5 structure, which results in the IRMOF-3 structure, is sufficient to increase dynamic ammonia capacity more than 18-fold. Though IRMOF-62 has some kinetic adsorption capacity, it too lacks any reactive functionality and is surpassed by BPL-carbon in almost all cases. All three of the aforementioned MOFs had little or no capacity for sulfur dioxide. One MOF to have demonstrated considerable capacity for chlorine gas is IRMOF-62, which is likely the result of the highly reactive nature of the gas. Even chlorine, against which the open metal site MOFs were ineffective. Clearly it is possible to adsorb a range of contaminants that will react either as Lewis acids or Lewis bases simply by including a reactive functionality of the opposite functionality in a MOF structure.

Some insight into the adsorption mechanism in MOFs can be gleaned by observing changes of color upon adsorption of the contaminants. Activated MOF-199 is deep violet in color. Upon exposure to the atmosphere, its color rapidly changes to light blue because water molecules coordinate to the open copper site. An identical color change is observed upon adsorption of ammonia, indicating that a similar adsorption process is occurring. The color change progresses through the adsorbent bed clearly indicating the progress of the ammonia front. The change is not reversed by prolonged flow of pure nitrogen, indicating that ammonia molecules have chemisorbed to the copper site. Similar color changes are observed upon exposure of MOF-74 to sulfur dioxide, IRMOF-3 to chlorine and ammonia, and IRMOF-62 to chlorine, each of which does not undergo a color change upon exposure to atmosphere. In each case the color change clearly indicates the progression of the contaminant front through the adsorbent bed and is not reversed by pure nitrogen flow. Observation of the adsorption process as a color change in the adsorbent is a possibility for MOFs that does not exist for BPL-carbon. It provides insight into the binding mechanism and gives a clear indication of the extent of saturation of the adsorbent.

Capture of Vaporous Contaminants.

Figure 3:
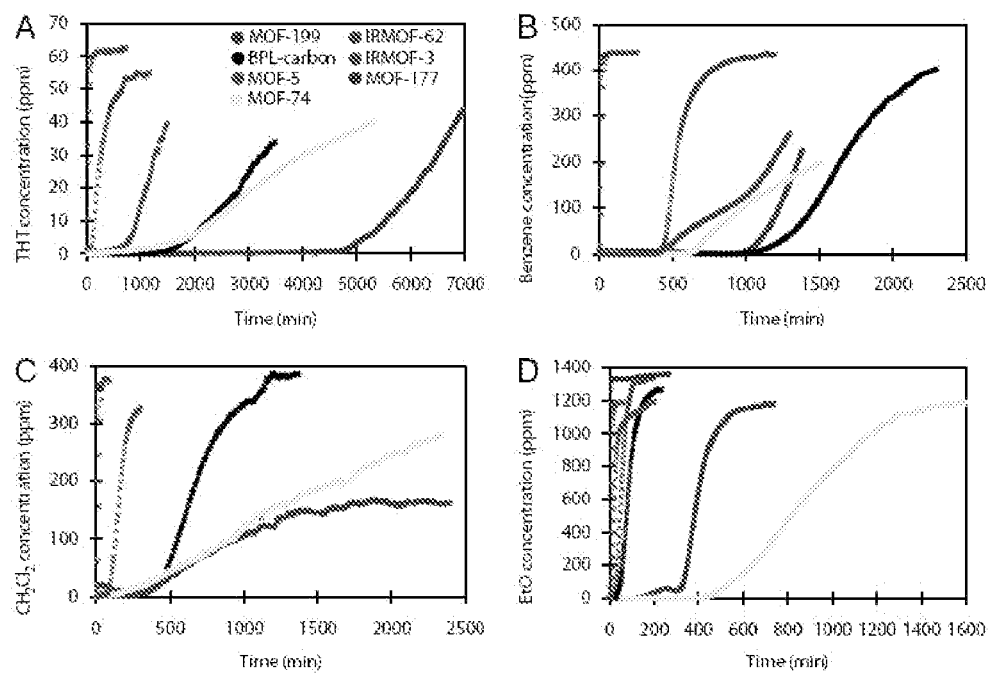
FIG. 3 shows breakthrough curves of vaporous (a) tetrahydrothiophene, (b) benzene, (c) dichloromethane and (d) ethylene oxide in the benchmark MOFs.
Figure 4:
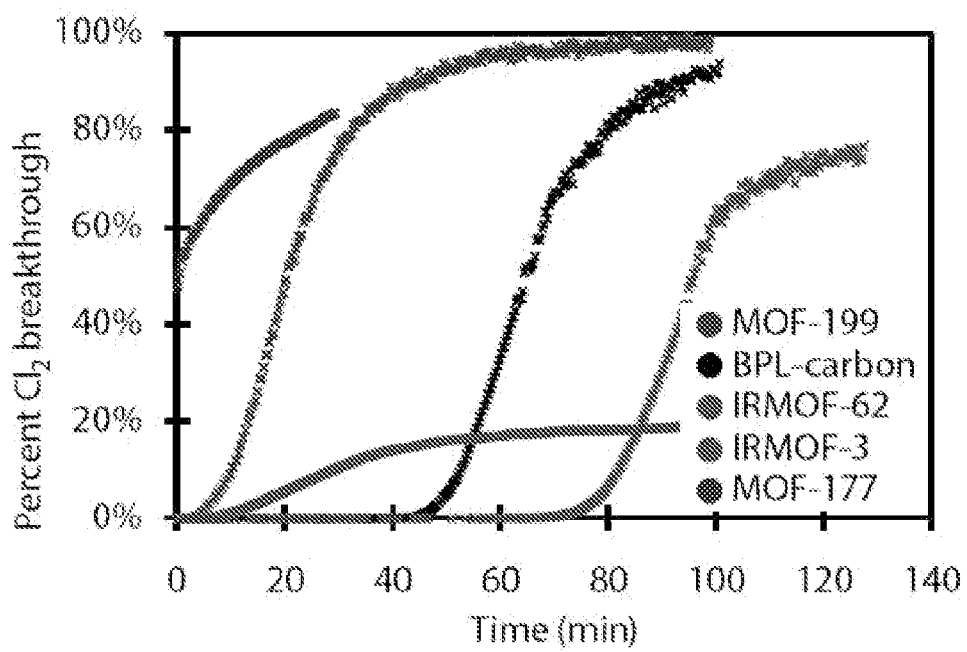
FIG. 4 shows chlorine breakthrough curves.
Figure 5:
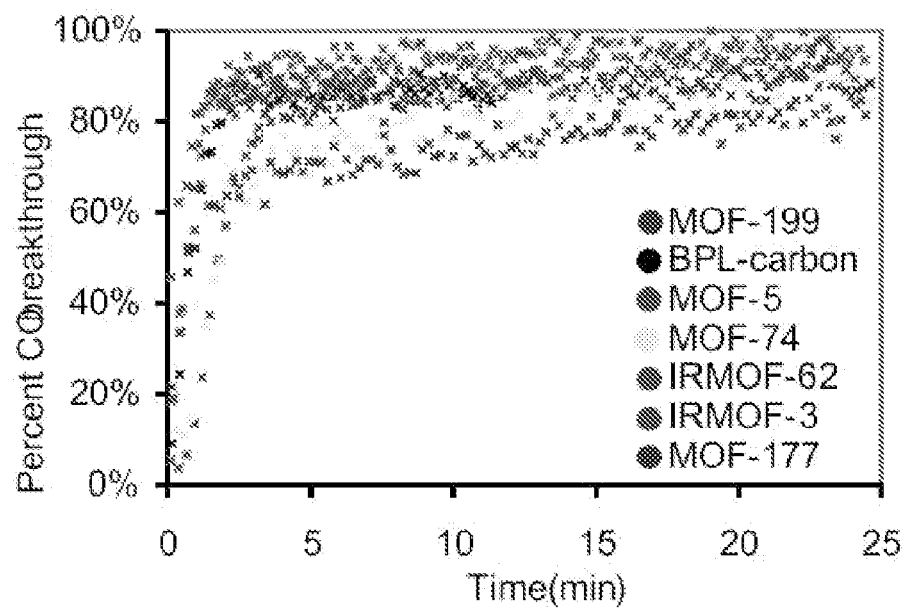
FIG. 5 shows carbon monoxide breakthrough curves.
Figure 6:
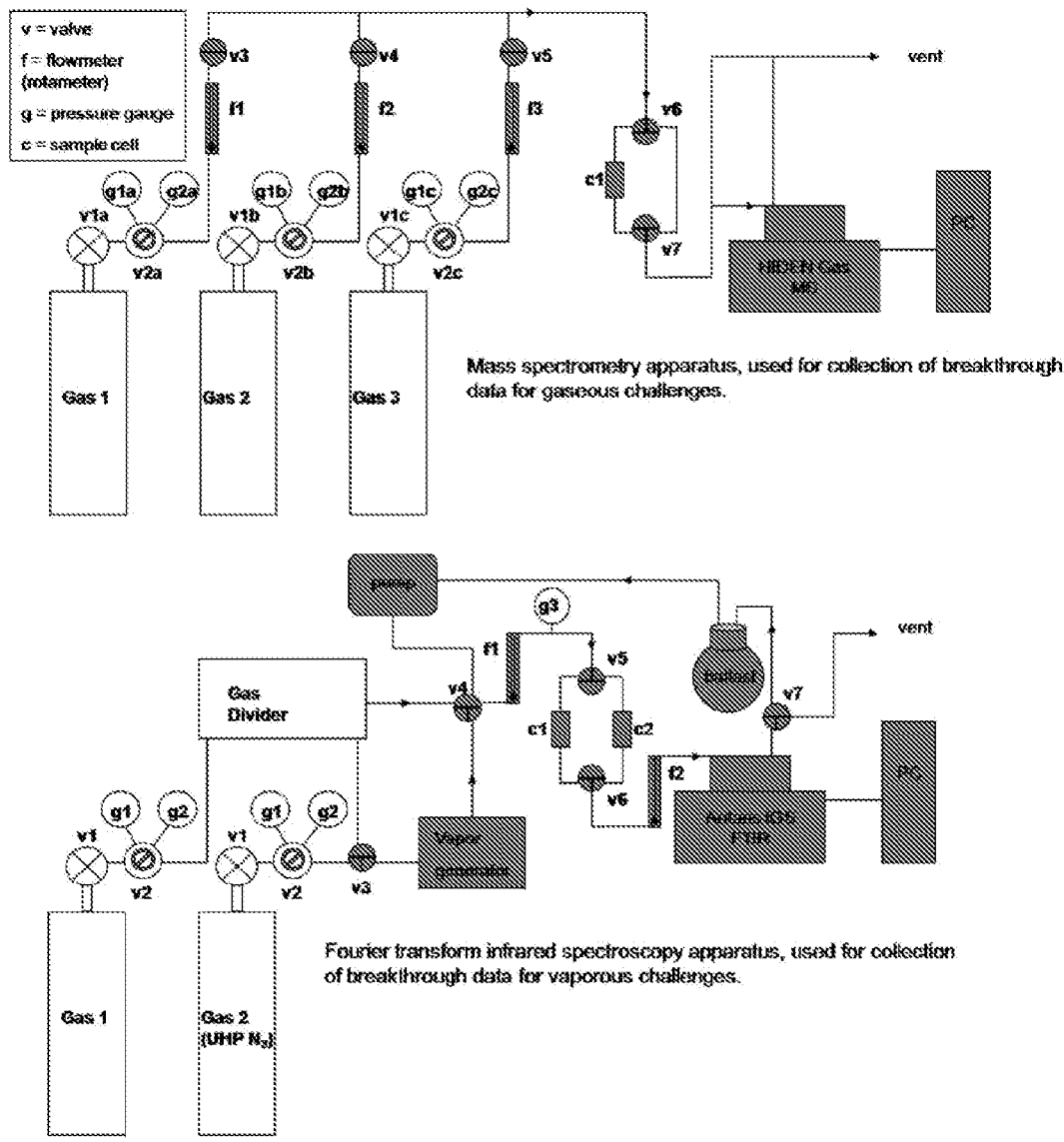
FIG. 6 shows apparatus used in the collection of breakthrough data for gaseous (Upper) and vaporous (Lower) challenges.

Breakthrough curves for tetrahydrothiophene, benzene, dichloromethane, and ethylene oxide were recorded using the benchmark MOFs and BPL-carbon. Plots of the breakthrough curves and estimated dynamic adsorption capacities for gaseous contaminants are presented in FIG. 3 and Table 2, respectively.

In following with the results of breakthrough experiments on gaseous contaminants, MOF-5 and MOF-177 do not perform well as kinetic adsorption media. IRMOF-62 is also largely outclassed by BPL-carbon except in the case of ethylene oxide adsorption, where IRMOF-62 and BPL-carbon are equally ineffective. IRMOF-3 is a poor adsorbent for the vapors chosen, as none behave as good Lewis acids.

Open metal sites, particularly the copper sites found in MOF-199, prove to be the most effective in removing vapors from the gas stream. Both MOF-74 and MOF-199 outperform BPL-carbon by an order of magnitude. However, MOF-74 is not effective against the entire range of vapors, while MOF-199 is. There is essentially no difference in performance between the activated carbon and MOF-199 in dichloromethane adsorption. There is some improvement over BPL-carbon in benzene adsorption and improvement by nearly a factor of 3 in adsorption of tetrahydrothiophene. In each case except dichloromethane MOF-199 exhibits a color change identical to that observed upon exposure to water or ammonia, again indicating a strong interaction with the open copper site.

Figure 7:
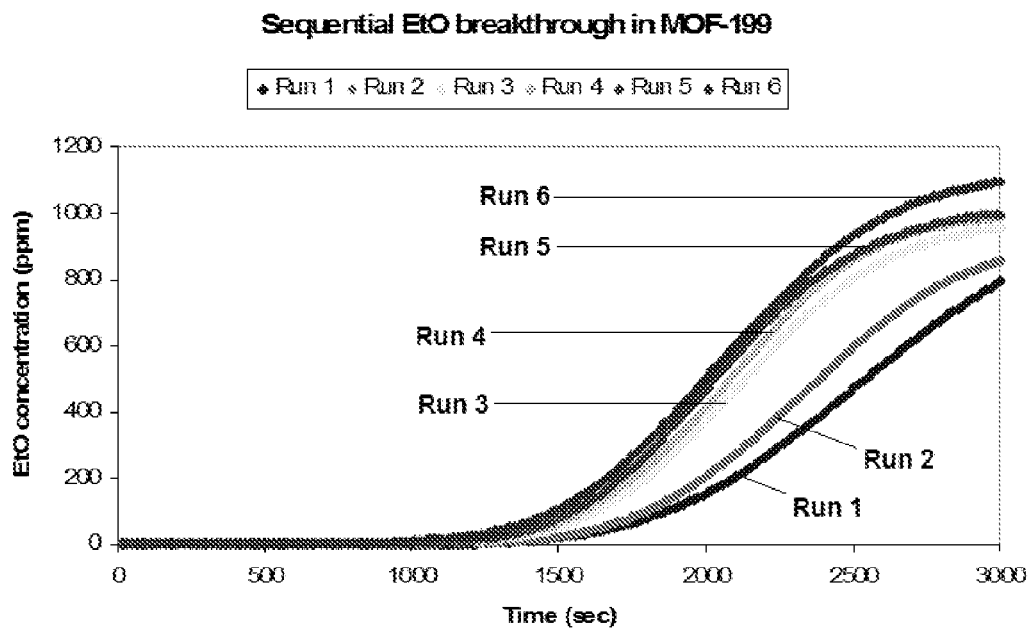
FIG. 7 shows a graph of sequential ethylene oxide (EtO) breakthrough curves using MOF-199.
Figure 8:
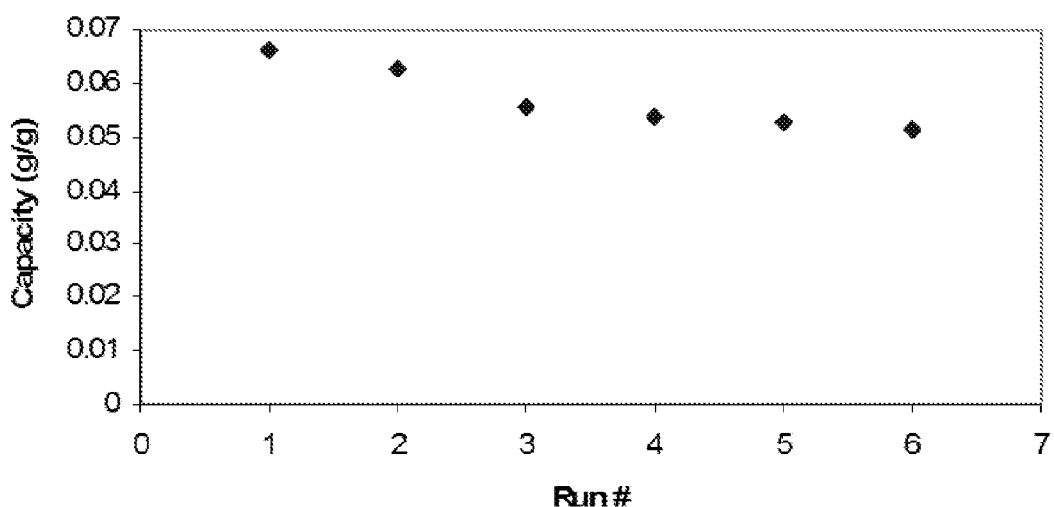
FIG. 8 shows a graph of ethylene oxide (EtO) capacity using MOF-199 in sequential runs.

Additional experiments were performed to analyze the adsorption of ethylene oxide to one of the MOFs described herein, MOF-199. FIG. 7 shows a series of breakthrough experiments using ethylene oxide and MOF-199. The breakthrough experiment is repeated on the same sample of MOF after blowoff of the previously adsorbed ethylene oxide. What is demonstrated is that the capacity of the MOF is substantially retained (e.g., within 400 ppm) over a series of runs. The second figure expresses the runs as gram per gram uptake, indicating that the MOF takes up in the range of about 5 wt. percent.

The examples above are intended to further describe certain element of the disclosure and are not intended to limit the invention as described by the following claims.

What is claimed is:

1. A method of separating ethylene oxide in a fluid or gas mixture comprising contacting the fluid or gas mixture with a porous metal organic framework comprising coordinatively unsaturated metal sites that can form a bond with ethylene oxide without causing ethylene oxide to undergo ring opening, wherein the ethylene oxide is absorbed or adsorbed to the porous metal organic framework, and wherein the ethylene oxide can be recovered from the porous framework.

2. The method of claim 1, comprising a replaceable guest species within the porous metal organic framework.

3. The method of claim 1, wherein the porous metal organic framework comprises a plurality of unsaturated metals linked by a trimesate linking moiety.

4. The method of claim 3, wherein the porous metal organic framework comprises MOF-199.

5. The method of claim 1, wherein the porous metal framework has an adsorption capacity of 4% or more by weight for ethylene oxide.

6. The method of claim 1, wherein the ethylene oxide can be recovered from the porous framework by changing the pressure and/or temperature.

7. The method of claim 1, wherein the porous metal organic framework comprises MOF-74.

8. A method of separating ethylene oxide in a mixed fluid or gas comprising contacting a device comprising a porous framework having coordinatively unsaturated metal sites that can form a bond with ethylene oxide without causing ethylene oxide to undergo ring opening, wherein the porous framework adsorbs or absorbs ethylene oxide, and wherein the ethylene oxide can be recovered from the porous framework with the mixed fluid or gas, wherein the ethylene oxide is absorbed or adsorbed to the porous metal organic framework thereby separating the ethylene oxide from the mixed fluid or gas.

9. The method of claim 8, wherein the device comprises a fixed bed of the porous metal organic framework.

10. The method of claim 8, wherein the device is a pressure-swing adsorption device.

11. The method of claim 8, wherein the porous framework is MOF-199, MOF-74, or a combination thereof.

12. A filtration system comprising a mixed fluid or gas containing ethylene oxide, a gas or fluid inlet and an outlet; a metal organic framework (MOF) thereof disposed between the inlet and the outlet, wherein the MOF comprises coordinatively unsaturated metal sites that can form a bond with ethylene oxide without causing ethylene oxide to undergo ring opening, wherein the mixed fluid or gas comprising ethylene oxide enters the inlet and contacts the MOF as it flows towards the outlet, and wherein the fluid or gas is substantially depleted of ethylene oxide at the outlet.

13. The filtration system of claim 12, wherein the system comprises a fixed bed system.

14. The filtration system of claim 12, wherein fluid flow is a linear flow.

15. The filtration system of claim 12, wherein the system comprises a pressure swing adsorption system.

16. The filtration system of claim 12, wherein the system comprises a temperature swing adsorption system.

* * * * *

UNITED STATES PATENT AND TRADEMARK OFFICE
CERTIFICATE OF CORRECTION

PATENT NO. : 8,709,134 B2  
APPLICATION NO. : 13/147357  
DATED : April 29, 2014  
INVENTOR(S) : Yaghi et al.

Page 1 of 1

It is certified that error appears in the above-identified patent and that said Letters Patent is hereby corrected as shown below:

Title Page, Item (75) Inventors, should read

--(75) Inventors: Omar M. Yaghi, Berkeley, CA (US); David Kyle Britt, El Cerrito, CA (US); Alexander U. Czaja, Freinsheim (DE); Torsten Maeurer, Lambsheim (DE)--.

Signed and Sealed this  
Twenty-first Day of June, 2016

Michelle K. Lee  
*Director of the United States Patent and Trademark Office*